(12) United States Patent
Jing

(10) Patent No.: US 7,772,511 B2
(45) Date of Patent: Aug. 10, 2010

(54) ELECTRIC POWER SOCKET MODULE

(75) Inventor: Jinbo Jing, Dong-Guan (CN)

(73) Assignee: Delta Electronics, Inc., Taoyuan (TW)

( * ) Notice: Subject to any disclaimer, the term of this patent is extended or adjusted under 35 U.S.C. 154(b) by 0 days.

(21) Appl. No.: 12/415,107

(22) Filed: Mar. 31, 2009

(65) Prior Publication Data

US 2010/0175978 A1  Jul. 15, 2010

(30) Foreign Application Priority Data

Jan. 9, 2009  (TW) .............................. 98200327 A

(51) Int. Cl.
*H01R 13/70* (2006.01)
(52) U.S. Cl. ................................. 200/51 R; 200/51.11

(58) Field of Classification Search ............... 200/51 R, 200/51.11, 51.12; 307/116, 117, 140; 439/11, 439/651, 652, 620, 606, 910, 490, 106, 76.1, 439/76.2, 740, 949
See application file for complete search history.

(56) References Cited

U.S. PATENT DOCUMENTS

| | | | | |
|---|---|---|---|---|
| 6,201,197 B1 * | 3/2001 | Mori et al. | ................. | 200/51 R |
| 6,215,080 B1 * | 4/2001 | Mori et al. | ................. | 200/51 R |
| 6,515,851 B1 * | 2/2003 | Ootori et al. | ........... | 361/679.08 |
| 6,802,741 B1 * | 10/2004 | Shatkin | ................. | 439/620.21 |
| 7,547,853 B2 * | 6/2009 | Lin et al. | ................... | 200/51 R |

* cited by examiner

*Primary Examiner*—Michael A Friedhofer
(74) *Attorney, Agent, or Firm*—Grossman, Tucker, Perreault & Pfleger, PLLC

(57) ABSTRACT

An electric power socket module comprising a socket portion, a switch portion and a plurality of conductive pins is provided. The socket portion and the switch portion are integrally formed and electrically connected in series by using the conductive pins. Thus, conventional wirings and hand-welding can be eliminated to reduce the costs and enhance safety.

5 Claims, 3 Drawing Sheets

ELECTRIC POWER SOCKET MODULE

This application claims priority to Taiwan Patent Application No. 098200327 filed on Jan. 9, 2009.

CROSS-REFERENCES TO RELATED APPLICATIONS

Not applicable.

BACKGROUND OF THE INVENTION

1. Field of the Invention

The present invention provides an electric power socket module, and more particularly, an electric power socket module with a switch.

2. Descriptions of the Related Art

The host of a personal computer is generally comprised of a power supply, a main board, a central processing unit (CPU), a memory, an optical disc drive, a hard disc drive and a housing, wherein the power supply is configured to supply a stable operation voltage to maintain the continuous operation of the aforesaid operational components.

Generally, even when the personal computer is powered off, the power supply still outputs a standby voltage to the main board. The standby voltage not only consumes power, but also accelerates the aging of the internal components. As an option to have the personal computer consume no power in the power-off status, the power cord may simply be removed. However, the frequent plugging-in and removal of the power cord would cause a lot of trouble to the user unless the personal computer remains unused for an extended time period. Accordingly, in some conventional power supplies, an additional switch is disposed on the socket so that the electric power can be switched off completely without removing the power cord when the computer is not in use.

However, in conventional power supplies that have such a switch, the switch and the socket are formed separately and then assembled together, and common electric wirings are soldered between the socket, the switch and the circuit board. Hence, many problems in terms of the cost, the manufacturing processes and the safety still exist for such conventional structures. For example, using soldered electric wirings as materials for electrical connection results in high costs associated with both the materials and hand-soldering labor. An improper soldering process might lead to safety problems in use.

In view of this, this invention provides an electric power socket module with a switch and without the use of electric wirings.

SUMMARY OF THE INVENTION

The objective of this invention is to provide an electric power socket module that has a small volume and has a socket and switch formed integrally. Furthermore, this invention eliminates the use of electric wirings and the hand-soldering, which makes the manufacturing and assembling processes more convenient and time-saving. As a result, the material and labor costs are reduced, while the safety of the electric power socket module in use is improved.

This invention provides an electric power socket module, comprising a socket portion, a switch portion and a plurality of conductive pins. The electric power socket module is unique in that the socket portion and the switch portion are integrally formed; both the switch portion and the socket portion have a conductor and are electrically connected in series through the conductive pins. The conductive pins, which are preferably conductive strips that are flat and bendable, electrically connect the switch portion and the socket portion to the circuit board.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
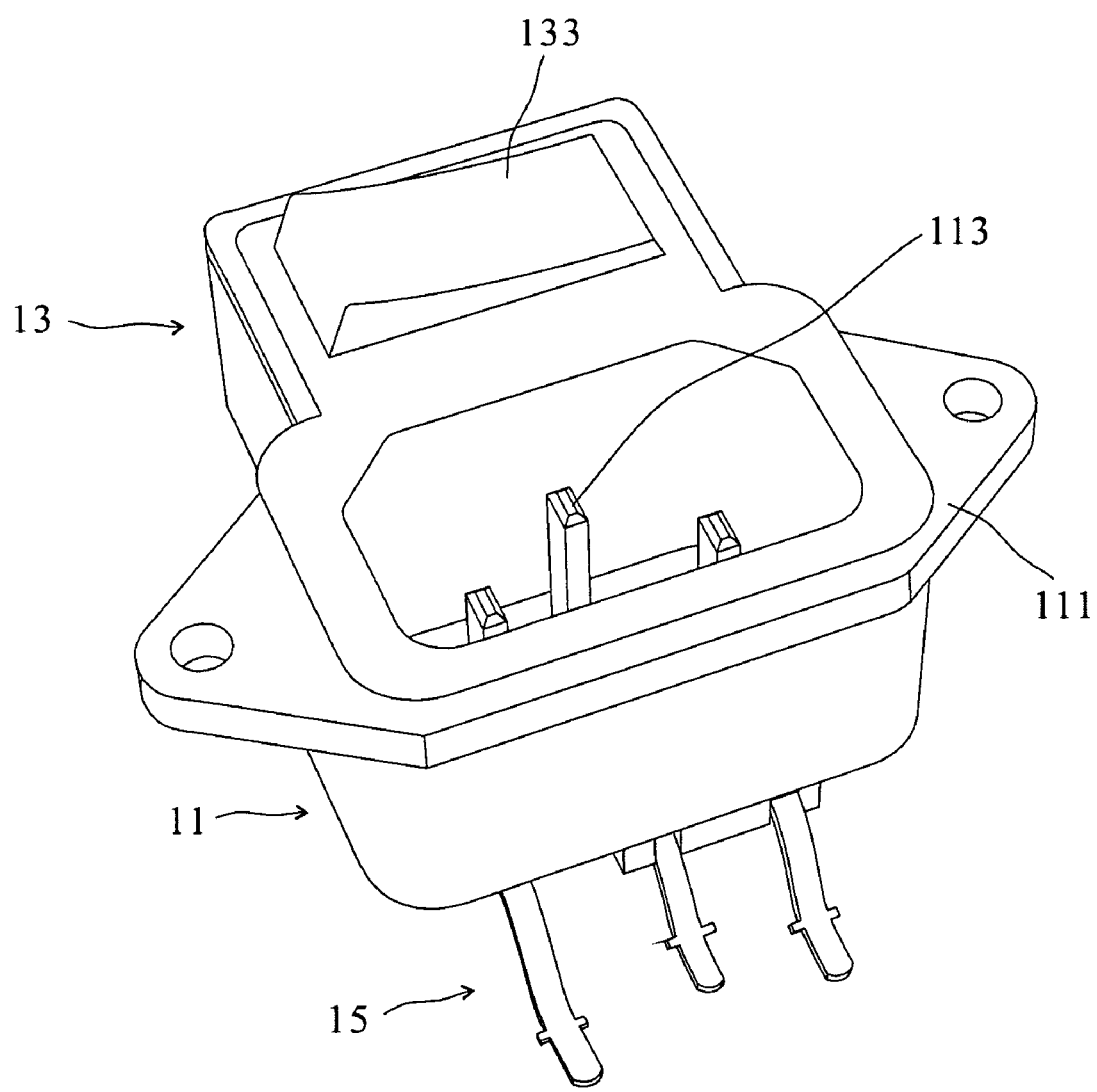
FIG. 1 is a perspective structural view of this invention.

What is described hereinbelow is merely a preferred embodiment, but not to limit the scope of this invention. FIG. 1 is a schematic view of an electric power socket module 1 of this invention, which comprises a socket portion 11, a switch portion 13 and a plurality of conductive pins 15. Unlike the electric wiring connections in the prior art, the conductive pins 15 of this invention are preferably conductive strips that are flat and bendable. The socket portion 11 and the switch portion 13 are formed integrally. Both the switch portion 13 and the socket portion 11 have a conductor (e.g., a contact plate or other conductive structures), and are electrically connected in series via the conductive pins 15.

Figure 2:
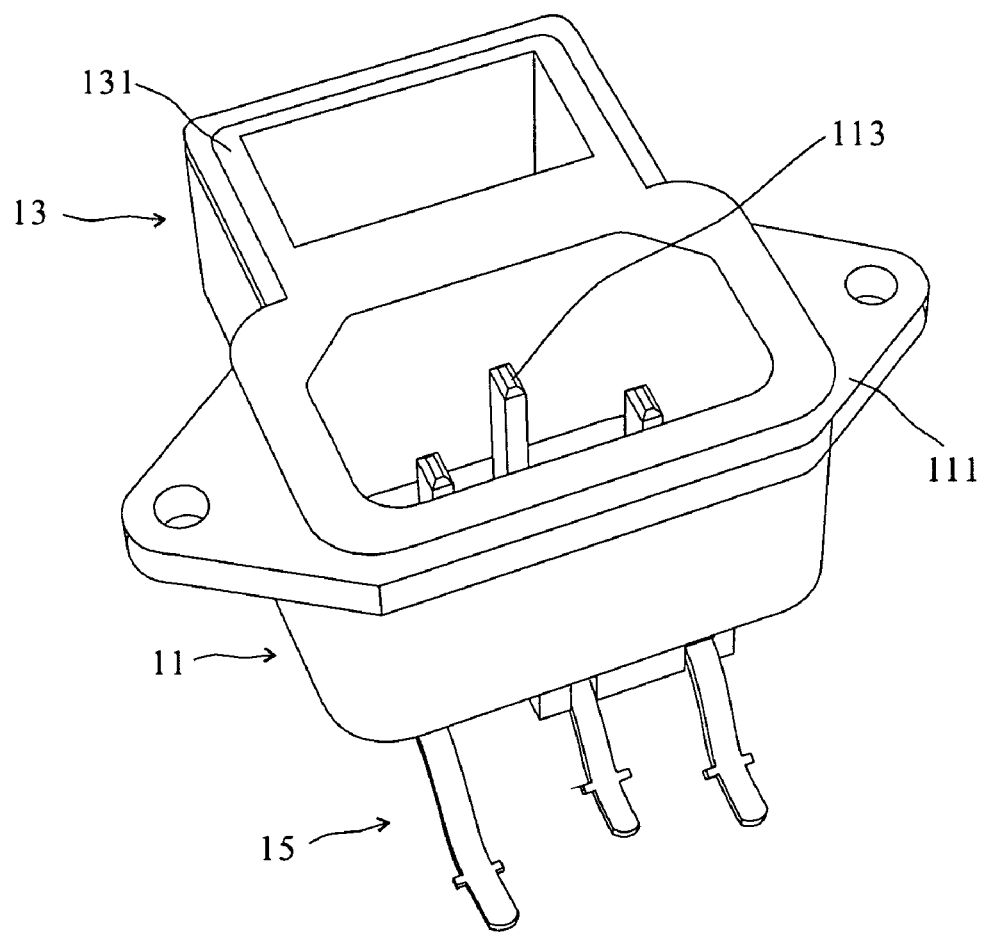
FIG. 2 is a perspective structural view of this invention when a switch is uninstalled.

The socket portion 11 comprises a socket housing 111 and a conductive portion 113 disposed in the socket housing 111. The switch portion 13 comprises a switch housing 131 and a switch controller 133 disposed in the switch housing 131. In this embodiment, the socket housing 111 and the switch housing 131 are integrally formed, as shown in FIG. 2. The integrally forming process may be accomplished by, for example, an injection molding or cast molding process; this will be appreciated by those of ordinary skill in the art and can be readily replaced by other manufacturing processes, so no limitation is made herein.

Figure 3:
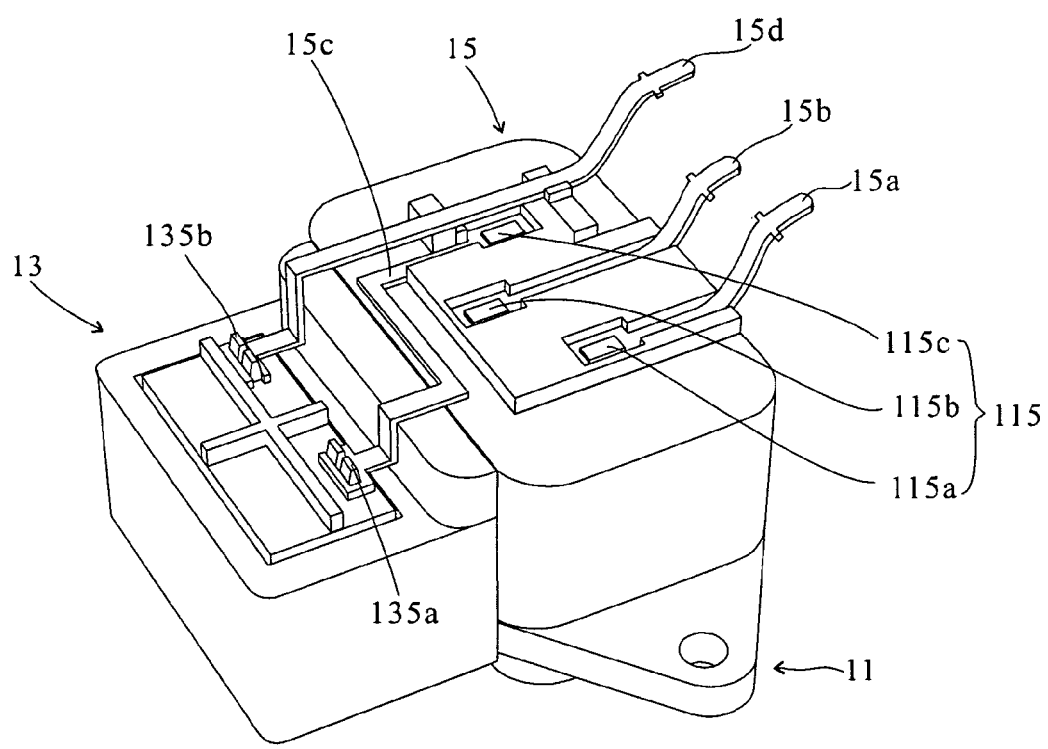
FIG. 3 is a perspective rear view of this invention.

In the socket portion 11, the conductive portion 113 comprises three common male conductive elements and a plurality of socket contact plates 115 disposed on the bottom of the socket housing 111, as shown in FIG. 3, and is connected with the male conductive elements respectively. It should be noted that the conductive portion 113 may only comprise two socket contact plates 115, in which case the electric power socket module 1 of this invention is a socket without a ground terminal.

The switch controller 133 mainly comprises a switch button, two switch contact plates 135a, 135b and an elastic element (not shown). The switch contact plates 135a, 135b are disposed on the bottom of the switch housing 131, and the switch button controls the conduction to the switch contact plates by the elastic element so that operating the switch controller 133 may control the On/Off status of the switch portion.

More specifically, in this embodiment, the two socket contact plates 115a, 115b are electrically connected to a circuit board (not shown) via the two conductive pins 15a, 15b respectively. Another socket contact plate 115c is connected to one of the switch contact plates 135a through the conductive pin 15c, while the other switch contact plate 135b of the switch portion 13 is electrically connected to the circuit board through another conducting pin 15*d*. In this way, the socket portion 13, the switch portion 11 and the circuit board can be electrically connected in series under the control of the switch controller 133.

According to the above descriptions, the electric power socket module disclosed in this invention has a socket and a switch formed integrally and eliminates the use of electric wirings and the hand-soldering process, which makes the assembly process more convenient and time-saving. As a result, manufacturing costs associated with the materials and labor are reduced, while the safety of the electric power socket module in use is improved.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An electric power socket module, comprising a socket portion, a switch portion and a plurality of conductive pins, characterized in that the socket portion and the switch portion are integrally formed, and the switch portion electrically connects to the socket portion in series through the conductive pins, wherein the socket portion comprises a conductive portion and the switch portion comprises a switch controller, wherein the conductive portion comprises a plurality of socket contact plates and the switch controller comprises two switch contact plates, in which two of the socket contact plates are electrically connected to a circuit board through two of the conductive pins respectively, another socket contact plate is connected to one of the switch contact plates through one of the conductive pins, and the other switch contact plate is electrically connected to the circuit board through another one of the conducting pins.

2. The electric power socket module as claimed in claim 1, wherein each of the conducting pins is conductive strip being flat and bendable.

3. The electric power socket module as claimed in claim 1, wherein the socket portion comprises a socket housing for the conductive portion being disposed therein, and the switch portion comprises a switch housing for the switch controller being disposed therein, in which the socket housing and the switch housing are integrally formed.

4. The electric power socket module as claimed in claim 3, wherein the two switch contact plates are disposed on a bottom of the switch housing and electrically connected to the conductive pins respectively, the switch controller further comprising an elastic element and a switch button controlling the conduction to the switch contact plates by the elastic element.

5. The electric power socket module as claimed in claim 4, wherein the conductive portion comprises three male conductive elements, the plurality of socket contact plates being disposed on a bottom of the socket housing and connected with the male conductive elements respectively.

\* \* \* \* \*